United States Patent
Lindsay et al.

(10) Patent No.: US 11,497,902 B2
(45) Date of Patent: Nov. 15, 2022

(54) CATHETER COUPLER AND METHODS OF EXCHANGING CATHETERS

(71) Applicant: Merit Medical Systems, Inc., South Jordan, UT (US)

(72) Inventors: Richard Lindsay, Belfast (IE); Kirk Loren Foote, Cottonwood Heights, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 37 days.

(21) Appl. No.: 16/549,574

(22) Filed: Aug. 23, 2019

(65) Prior Publication Data
US 2020/0061363 A1 Feb. 27, 2020

Related U.S. Application Data

(60) Provisional application No. 62/722,419, filed on Aug. 24, 2018.

(51) Int. Cl.
*A61M 39/10* (2006.01)
*A61M 27/00* (2006.01)

(52) U.S. Cl.
CPC ............ *A61M 39/10* (2013.01); *A61M 27/00* (2013.01); *A61M 2205/0238* (2013.01); *A61M 2205/32* (2013.01); *A61M 2205/583* (2013.01)

(58) Field of Classification Search
CPC .................. A61M 27/00; A61M 39/10; A61M 2025/0163; A61M 2205/32; A61M 2205/0238; A61M 2205/583; A61M 2039/087
See application file for complete search history.

(56) References Cited

U.S. PATENT DOCUMENTS

| | | | | |
|---|---|---|---|---|
| 5,549,554 A | * | 8/1996 | Miraki | A61M 25/00 604/101.05 |
| 2005/0192638 A1 | * | 9/2005 | Gelfand | A61N 1/3605 607/3 |
| 2006/0284423 A1 | | 12/2006 | Katsuno et al. | |
| 2007/0241119 A1 | | 10/2007 | Durkin et al. | |

(Continued)

FOREIGN PATENT DOCUMENTS

WO 2018085566 A2 5/2018

OTHER PUBLICATIONS

European Search Report dated May 2, 2022 for EP19852805.1.

*Primary Examiner* — Tatyana Zalukaeva
*Assistant Examiner* — Nhu Q. Tran
(74) *Attorney, Agent, or Firm* — Dorsey & Whitney LLP

(57) ABSTRACT

The present disclosure relates to a catheter coupler and methods of exchanging catheters within a patient with a replacement catheter. The catheter coupler is configured to couple to a first catheter that has been disposed within a patient and coupled to a second or replacement catheter. Once the coupler is coupled to the first and second catheter, the first catheter may be withdrawn from the patient, which simultaneously advances the second or replacement catheter into the previous position of the first catheter. The coupler may include a body with a first end and a second end. The coupler may have a plurality of barbs disposed on both ends of the body of the coupler, wherein the barbs are configured to couple the coupler to the lumen of the catheters.

17 Claims, 15 Drawing Sheets

(56) References Cited

U.S. PATENT DOCUMENTS

| | | | |
|---|---|---|---|
| 2008/0021415 A1* | 1/2008 | Durkin | B29C 45/14598 |
| | | | 604/246 |
| 2008/0125696 A1* | 5/2008 | Callahan | A61M 1/84 |
| | | | 604/35 |
| 2009/0139529 A1 | 6/2009 | Worley | |
| 2010/0076410 A1* | 3/2010 | Ring | A61M 39/10 |
| | | | 604/533 |
| 2010/0312227 A1* | 12/2010 | House | A61M 25/0017 |
| | | | 604/544 |
| 2015/0308598 A1 | 10/2015 | Lewis et al. | |
| 2016/0158523 A1* | 6/2016 | Helm | A61M 39/10 |
| | | | 604/513 |
| 2018/0153552 A1* | 6/2018 | King | A61B 17/083 |
| 2019/0290896 A1* | 9/2019 | Phillips | A61M 39/12 |

\* cited by examiner

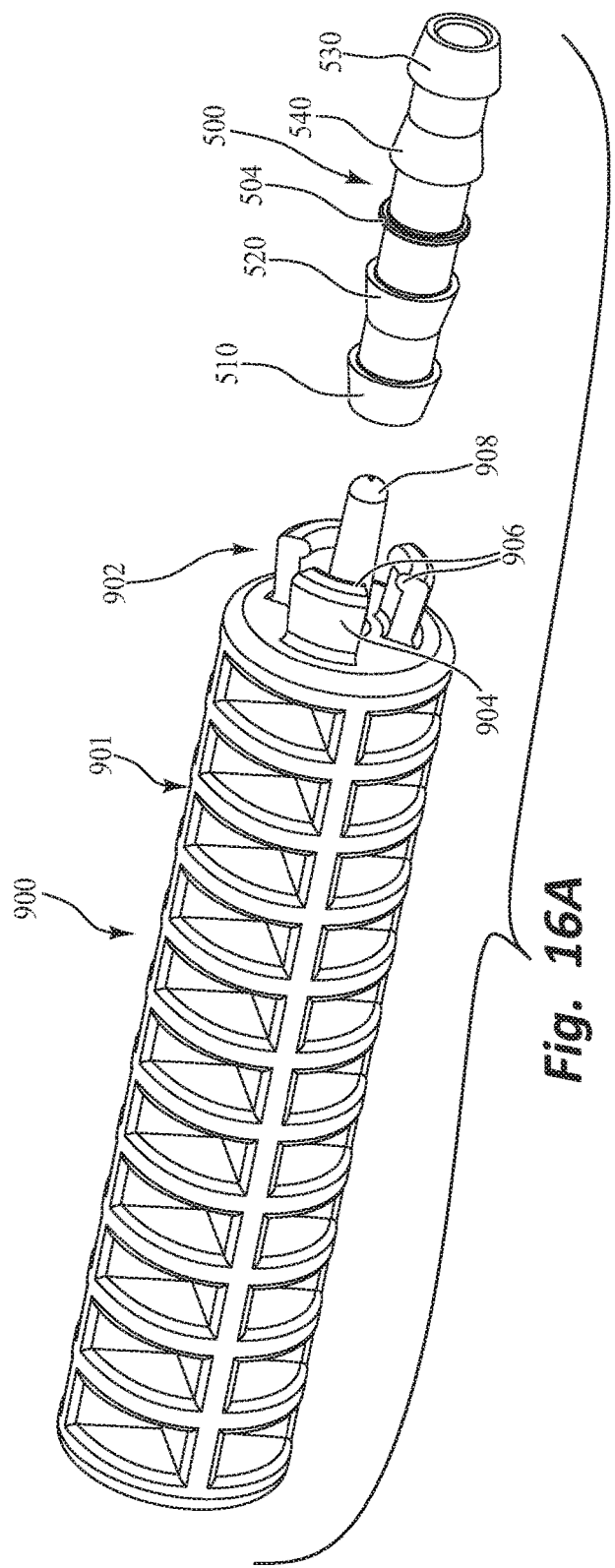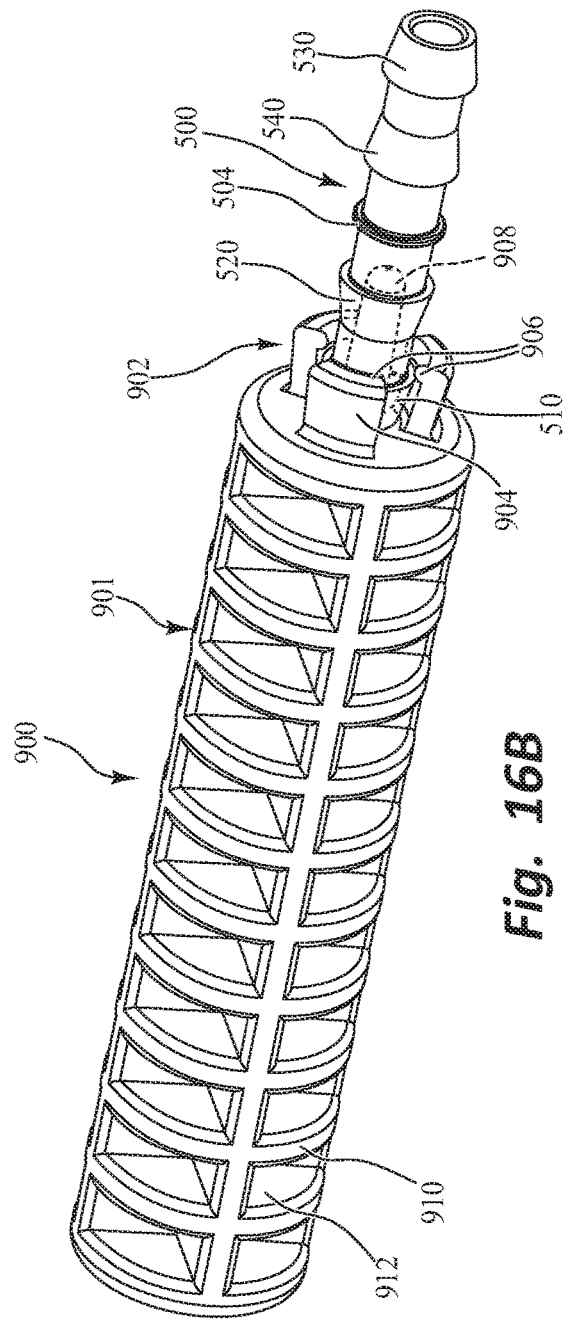

CATHETER COUPLER AND METHODS OF EXCHANGING CATHETERS

RELATED CASES

This application claims priority to U.S. Provisional Application No. 62/722,419, filed on Aug. 24, 2018, and titled "Catheter Coupler and Methods of Exchanging Catheters," which is hereby incorporated by reference in its entirety.

TECHNICAL FIELD

The present disclosure relates generally to drainage catheters for medical use. More specifically, the present disclosure relates to a looped drainage catheter and methods of exchanging drainage catheters.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

FIG. 16A is a perspective exploded view of a coupler delivery system, according to another embodiment.

FIG. 16B is a perspective view of the coupler delivery system of FIG. 16A in an assembled state.

DETAILED DESCRIPTION

Figure 1A:
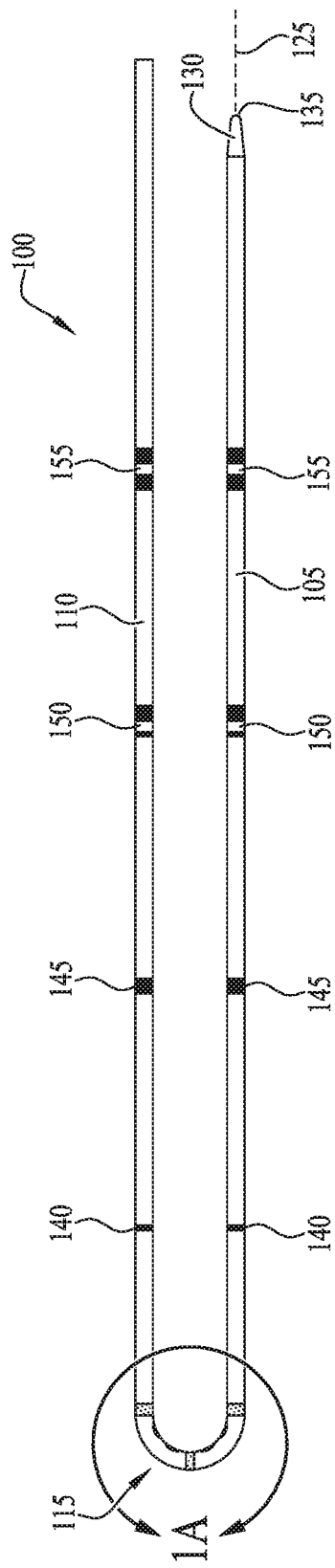
FIG. 1A illustrates a view of a looped drainage catheter in accordance with one embodiment.

The various embodiments disclosed herein generally relate to, but are not limited to, drainage catheters and related methods of use. More specifically, the various embodiments relate to a drainage catheter that may be used for percutaneous nephrostomy or nephropyelostomy, including providing temporary drainage for an obstructed renal collecting system. In some instances, the obstructed area may become infected, and antibiotics may have limited efficacy reaching the kidney if the obstruction is not drained. Percutaneous nephrostomy may be used to alleviate the obstruction and to create a route for antibiotic instillation and/or other treatments, if needed. As explained in further detail below, in some embodiments, the disclosed drainage catheter may be sufficiently pliable to minimize potential injury during insertion, but also sufficiently rigid to maintain a generally U-shape bend when deployed within the kidney, which may tend to avoid clogging and promote drainage. Also disclosed herein are methods for inserting the drainage catheter into a patient's kidney and methods of exchanging drainage catheters. The specific examples included herein are presented by way of example, the present disclosure may be applied to other catheter applications.

Various features are sometimes grouped together in a single embodiment, figure, or description thereof for the purpose of streamlining the disclosure. Many of these features may be used alone and/or in combination with one another.

Embodiments may be understood by reference to the drawings, wherein like parts are designated by like numerals throughout. The components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "distal" and "proximal" refer to opposite ends of a medical device, including the coupler disclosed herein, as well as the exemplary catheters. As used herein, the distal portion of the catheter is the portion that first enters the patient's body during insertion, while the proximal portion is a portion at the opposite end, along the longitudinal direction of the catheter.

The term "resilient" refers to a component, device, or object having a particular shape that can then be elastically deformed into a different shape, but that may return to the original shape when unconstrained. For example, a resilient portion of the catheter may have a first shape when unconstrained (i.e., when no exterior force acts upon the catheter) and, in use, the resilient portion may then be constrained (i.e., temporarily engaged with a guidewire) to elastically deform the resilient element into a second shape (i.e., a straightened condition over the guidewire). After the catheter is disposed in the kidney, the guidewire may be removed and the catheter may return to its first shape (unconstrained) or substantially to its first shape.

While the written description and figures may reference use of the catheter for percutaneous nephrostomy, the catheter may be used for providing drainage to other organs or anatomical structures, as well as for infusion of medication. Accordingly, the particular uses of the catheter outlined herein are meant as examples and not meant to limit use of the catheter and/or the coupler disclosed herein, to nephrostomy or kidney placement.

Figure 5:
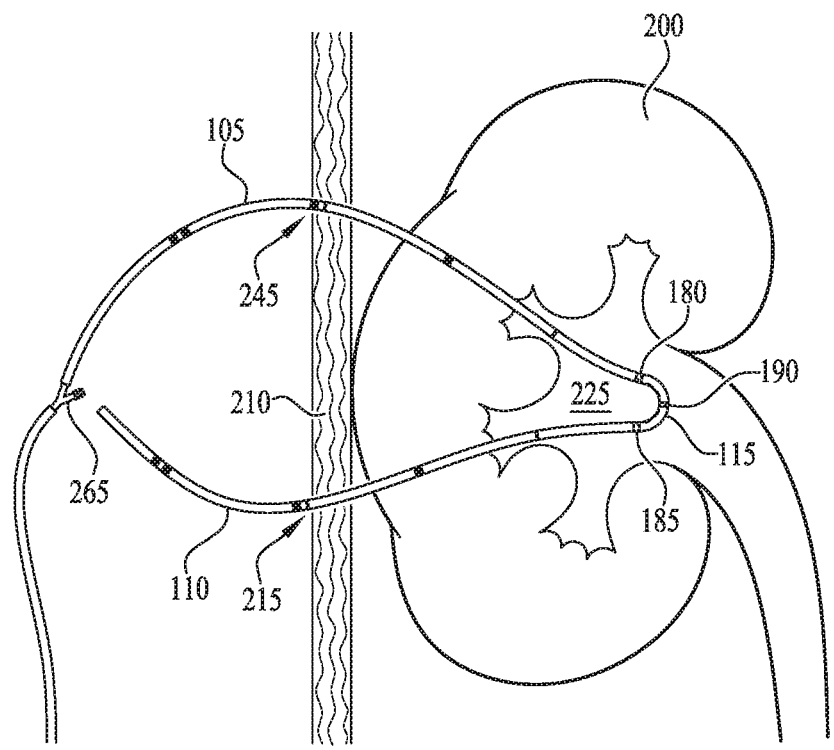
FIG. 5 illustrates the catheter of FIG. 1A in a deployed position.

FIG. 1A illustrates an embodiment of a drainage catheter 100 that may be used for percutaneous nephrostomy. With general reference to FIGS. 1A and 1B, the catheter 100 shown in these figures comprises a distal tube segment 105 and a proximal tube segment 110 connected together via a U-shaped or arcuate end portion 115. The arcuate end portion 115 may be generally U-shaped, as shown, or of another shape, as appropriate to the particular application. The catheter 100 may include a plurality of drainage holes or openings 175 formed along an inner surface 160 of the arcuate end portion 115. In some embodiments, the catheter 100 is free of drainage holes on an outer surface 165 to avoid clogging by surrounding kidney tissues or other structures. In an exemplary operation, once the catheter 100 is deployed within a kidney 200, the arcuate end portion 115 sits in a renal pelvis 225, with the tube segments 105, 110 each disposed outwardly through a skin 210 as illustrated in FIG. 5. The tube segments 105, 110 may be connected to a connector 265, which in turn is connected to a drainage bag or other receptacle (not shown) for collecting the drained material. The connector 265 may also include a port for infusing medication into the kidney 200 through the catheter 100.

With reference to FIG. 1A, the catheter 100 may comprise a generally elongate, tubular structure that may comprise any of a variety of materials, including resilient and flexible bio-compatible materials, such as silicone rubber, nylon, polyurethane, polyethylene terephthalate (PET), latex, thermoplastic elastomers, or other materials. As mentioned previously, the catheter 100 of FIG. 1A includes a distal tube segment 105 and a proximal tube segment 110 connected by an arcuate end portion 115 to form a continuous structure with a looped or reversing end. A lumen 120 may extend through the catheter 100 along a central axis 125 thereof to provide a passageway for fluids exiting the kidney. In some embodiments, the lumen 120 may also be used to introduce antibiotics or other fluids into the kidney as needed, such as to treat infections or to provide other medical relief. In some embodiments, a lead-in portion 130 of the distal tube segment 105 may be tapered or angled inwardly toward the central axis 125. Further, a lead end 135 of the distal tube segment 105 may be generally flat, resembling a truncated cone shape, with the lumen 120 extending therethrough. Preparatory to disposing the catheter 100 in a patient, the catheter 100 may be disposed upon a guidewire (see guidewire 230 in FIG. 4). As is further described below with reference to FIGS. 2-5, the lead-in portion 130 may be configured to facilitate advancement of the catheter 100 along the guidewire 230 during insertion into the kidney 200. In other embodiments, the lead-in portion 130 may not be tapered.

To facilitate and accurate placement of the catheter 100 within the kidney 200, the distal and proximal tube segments 105, 110 may each include various depth markers 140, 145, 150, 155 printed thereon at predetermined points along the catheter 100. In some embodiments, the depth markers 140, 145, 150, 155 encircle the circumference of the respective tube segments 105, 110. For example, with reference to FIG. 1A, the catheter 100 may include a 5-cm band marker 140, a 10-cm band marker 145, a 15-cm band marker 150, and a 20-cm band marker 155, with the respective markers printed on each of the tube segments 105, 110. In the illustrated embodiment, the position of the depth markers 140, 145, 150, 155 on the distal tube segment 105 mirrors the position of the depth markers 140, 145, 150, 155 on the proximal tube segment 110. In other embodiments, markers on each segment 105, 110 may not mirror each other. In some embodiments, the marking pattern associated with individual band markers may be unique for each particular depth marker to allow a practitioner to quickly determine the depth from the marking pattern alone rather than having to read a number scale or other numerical indicia. The depth values provided in the above description are for illustration purposes only. In other embodiments, the depth for the depth markers 140, 145, 150, 155 may be different from the scale noted above. In addition, the number of depth markers printed on the catheter 100 may be more or fewer than the four markers printed on the illustrated embodiment of the catheter 100, in some embodiments, the depth markers 140, 145, 150, 155 may include or be replaced by numeric symbols.

Figure 1B:
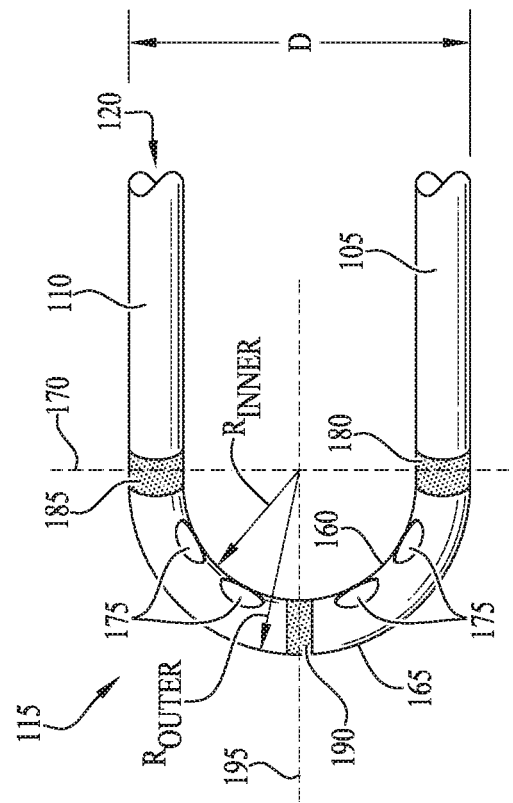
FIG. 1B illustrates a detailed view of an end portion of the looped drainage catheter of FIG. 1A.

With reference to FIG. 1B, the arcuate end portion 115 comprises an inner surface 160 and an outer surface 165. The inner surface 160 has a first radius of curvature $R_{inner}$ as measured from a transverse axis 170 generally traversing the catheter 100 at the edges of the arcuate end portion 115. The outer surface 165 has a second radius of curvature $R_{outer}$ measured relative to the transverse axis 170, with $R_{outer}$ being greater than $R_{inner}$.

The inner surface 160 of the arcuate end portion 115 may comprise a plurality of holes 175 formed thereon. The holes 175 may extend through the inner surface 160 of the catheter 100 such that they are in communication with the lumen 120. The holes 175 may thus be configured to provide a pathway for waste or other fluids out of the kidney and antibiotics and other medical fluids into the kidney. The holes 175 disposed on the inner surface 160 of the catheter 100 may allow guidewire passage through the catheter 100 without the need of fluoroscopy. In some embodiments, the outer surface 165 of the catheter 100 is free of holes. This absence of holes may be configured to minimize potential blockage and clogging of the holes to maintain patency of the catheter 100 as the kidney tissues press against the catheter 100. In other words, the body of the catheter 100 may tend to prevent tissue from collapsing against the holes 175 disposed along the inner surface 160 due to the arcuate shape of the catheter 100, thus helping maintain patency and prevent clogging.

The arcuate end portion 115 of the catheter 100 may further comprise radiopaque marker bands 180, 185, and 190 printed thereon to facilitate placement of the arcuate end portion 115 of the catheter 100 f. For example, with reference to FIG. 1B, the catheter 100 may include 2-mm wide marker bands 180, 185 generally mirroring one another on the tube segments 105 and 110 and marking the respective ends of the arcuate end portion 115, and include a 1.5-mm wide marker band 190 positioned at a general midpoint of the arcuate end portion 115 and along an arc neutral axis 195 of the arcuate end portion 115 generally perpendicular to the transverse axis 170. In some embodiments, the marker bands 180, 185, and 190 may be the same size, for example, 2 mm. In some embodiments, the marker bands 180 and 185 may be aligned on the transverse axis 170. In such embodiments, the marker band 190 may divide the position of the holes 175 to ensure an even distribution on the inner surface 160 of the catheter 100, with the marker bands 180, and 185 bookending the holes 175. In this arrangement, the marker bands 180, 185, and 190 collectively provide guidance to determine the position and arrangement of the holes 175 during and after insertion of the catheter 100. In addition, the number of marker bands may be more or fewer than the three marker bands 180, 185, and 190 on the illustrated embodiment of the catheter 100.

In some embodiments, the catheter 100 may include a hydrophilic coating on the catheter surface. The hydrophilic coating may absorb and bind water to promote a smooth and slippery surface and help reduce pain, pressure, or discomfort during the insertion and removal process. With reference to FIGS. 2-5, the following sections provide additional details of a process for inserting the catheter 100 during a percutaneous nephrostomy procedure according to one exemplary embodiment. Certain steps relating to a percutaneous nephrostomy procedure may not be discussed in detail, however, it is within the scope of this disclosure to use a coupler (see 300 in FIG. 6) along with a catheter 100 to exchange catheters placed according to a variety of procedures.

Figure 2:
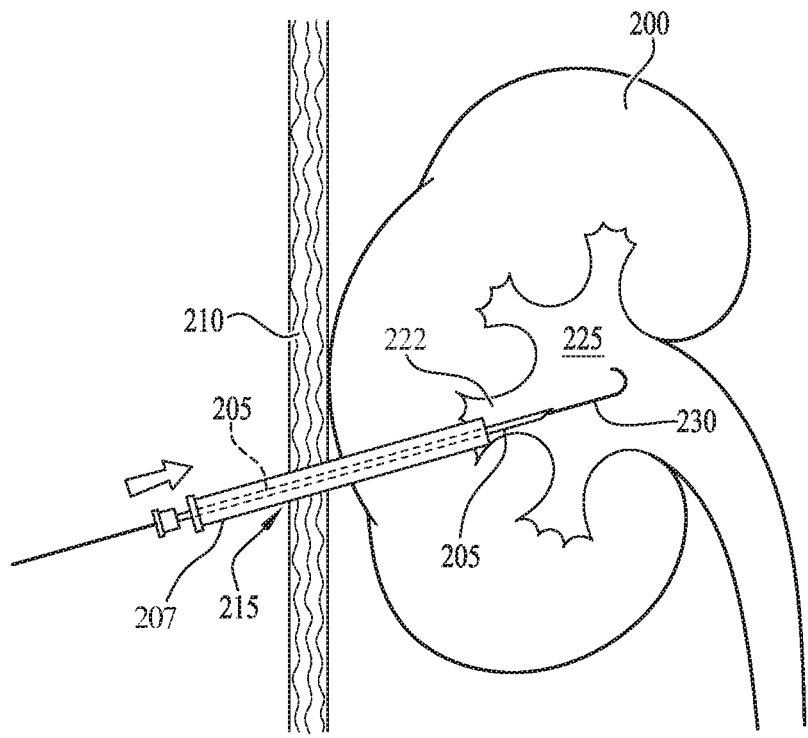
FIG. 2 illustrates a first needle and first guidewire positioned in the renal pelvis of the kidney.

FIGS. 2-5 illustrate an exemplary procedure for guiding and placing the catheter 100 within a kidney 200 during a percutaneous nephrostomy. With reference to FIG. 2, a first needle 205 housed within a first introducer sheath 207 may be used to puncture the skin 210 at a first insertion site 215. The needle 205 may then be pushed through a first calyx 222 to access the renal pelvis 225. With the first needle 205 in position, gentle suction may be placed on the first needle 205 until urine is aspirated to confirm placement. In some embodiments, the kidney 200 may be opacified with contrast to confirm the positioning of the catheter 100. The first needle 205 may be retracted from the first introducer sheath 207, and a guidewire 230 may be advanced through the first introducer sheath 207 and into the renal pelvis 225. In some embodiments, the guidewire 230 may include a hydrophilic coating to facilitate movement into the renal pelvis 225. In some embodiments, once the guidewire 230 is in position, the first introducer sheath 207 may be retracted, leaving the guidewire 230 in position. Alternatively, the first introducer sheath 207 may be left in position while the guidewire 230 is manipulated to couple with a snare 260 as described below. In certain embodiments, the first needle 205 may be used to puncture the skin 210 without the first introducer sheath 207 and the guidewire 230 may be advanced through the first needle 205.

Figure 3:
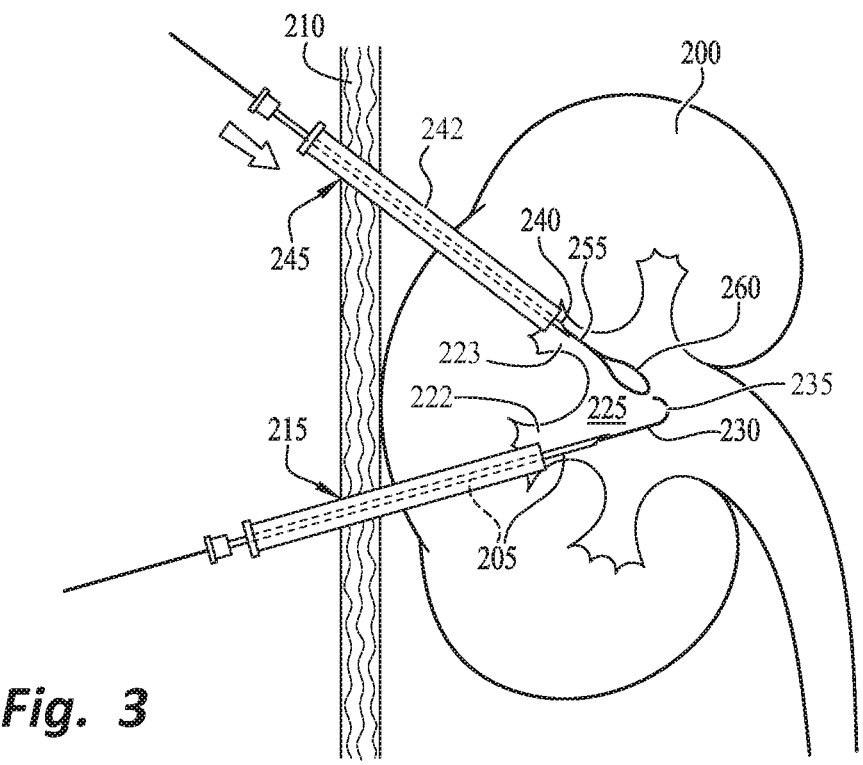
FIG. 3 illustrates a second needle and second guidewire having a snare to couple with the first guidewire.

With particular reference to FIG. 3, a second needle 240 housed within a second introducer sheath 242 may be used to puncture the skin 210 at a second insertion site 245 and pushed through a second calyx 223 toward the renal pelvis 225. The second introducer sheath 242 may then be positioned at the renal pelvis 225 near the guidewire 230, and the second needle 240 may be retracted from the second introducer sheath 242. A second guidewire 255 may be inserted through the second introducer sheath 242 and advanced toward the guidewire 230. An end of the second guidewire 255 may include the snare 260 or other grasping device configured to couple, to a portion of the guidewire 230 such as via a curved tip end 235. In embodiments where the guidewire 230 does not include the curved tip end 235 (e.g., the guidewire 230 may instead have a planar end), the snare 260 may be used to ensnare an end portion of the guidewire 230. Once the snare 260 is coupled to the guidewire 230, the second guidewire 255 may be retracted to advance the guidewire 230 such that the guidewire 230 extends from the first calyx 222 to the renal pelvis 225 and out the second calyx 223.

Figure 4:
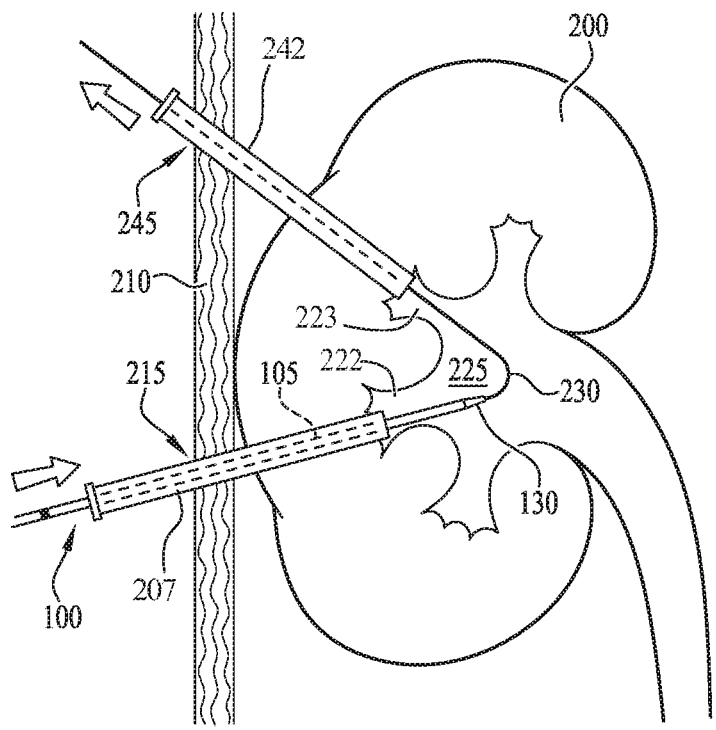
FIG. 4 illustrates the catheter of FIG. 1A partially advanced into the kidney over the first guidewire.

As generally illustrated in FIGS. 4 and 5, the catheter 100 may then be inserted into the kidney 200. With the guidewire 230 in position, the catheter 100 may first be straightened out to generally flatten out the arcuate end portion 115 for insertion. The lead-in portion 130 may be inserted onto the guidewire 230 and advanced along the guidewire 230 into the first calyx 222, through the renal pelvis 225, and out the second calyx 223. The catheter 100 may then be pulled outwardly through the second insertion site 245 until the arcuate end portion 115 is resting in a desired position within the renal pelvis 225. The radiopaque marker bands 180, 185, 190 may be used to position the holes 175. In some embodiments, a dilator (not shown) may be advanced over the guidewire 230 prior to insertion of the catheter 100 to further guide the catheter 100.

As noted previously, the arcuate end portion 115 may be resilient such that the arcuate end portion 115 rends to return to its initial curved configuration once the catheter 100 is free from external forces (see FIG. 5). The curvature of the arcuate end portion 115 and the placement of the holes 175 along the inner surface 160 may avoid clogging of the catheter 100 and promote drainage of the kidney 200 through the lumen 120.

With reference to FIG. 5, once the catheter 100 is positioned within the kidney 200, the first introducer sheath 207 and the second introducer sheath 242 may be removed. In addition, once the catheter 100 is positioned within the kidney 200, one or both of the tube segments 105 and 110 may be cut to a desired length to manage the catheter 100 as needed. For example, in one embodiment, the lead-in portion 130 of the distal tube segment 105 may be cut off and a connector 265 may be attached to both the distal and proximal tube segments 105 and 110 to direct fluids removed from the kidney 200 to a drainage bag or other receptacle (not shown). In some embodiments, the connecter 265 may include a port for the introduction of antibiotics or other medicine for infusion to the kidney 200. Further, the connector 265 may include a break-away portion that is removable to avoid damage that may be caused to the kidney 200 or other surrounding structures by accidental pulling or removal of the catheter 100. In some embodiments, the connector 265 may include break-away features such as those described in U.S. patent application Ser. Nos. 15/228, 796 and 15/802,160, the disclosures of which are incorporated herein by reference in their entirety.

In some embodiments, a pigtail nephrostomy catheter may be inserted into a kidney 200 of the patient through the first calyx 222 to access the renal pelvis 225. The pigtail nephrostomy catheter may not need dual access to the kidney 200 like the drainage catheter 100 and therefore the pigtail catheter may not exit the kidney 200 through the second calyx 223. The pigtail nephrostomy catheter may be inserted for a short-term nephrostomy, however, if a longer-term nephrostomy catheter is needed, the pigtail catheter may be replaced using a long-term nephrostomy catheter, such as the drainage catheter 100. If the pigtail catheter is replaced, the drainage catheter 100 may pass through the pre-existing tract into the kidney 200 made by the pigtail catheter and a fresh tract may be created to access the second calyx 223 so that the drainage catheter 100 may exit the patient.

Once disposed, over time the catheter 100 may become unsuitable to the purpose of emplacement. For example, the holes 175 or the lumen 120 may become blocked, or the patient may respond adversely to the material of which the catheter 100 is manufactured, or another medical treatment may require replacement of the particular catheter 100 with a different catheter. Rather than withdraw the catheter 100 and repeat the initial emplacement procedure with a new catheter, in some procedures a coupler (such as 300 of FIG. 6) may facilitate replacing the catheter 100.

Figure 6:
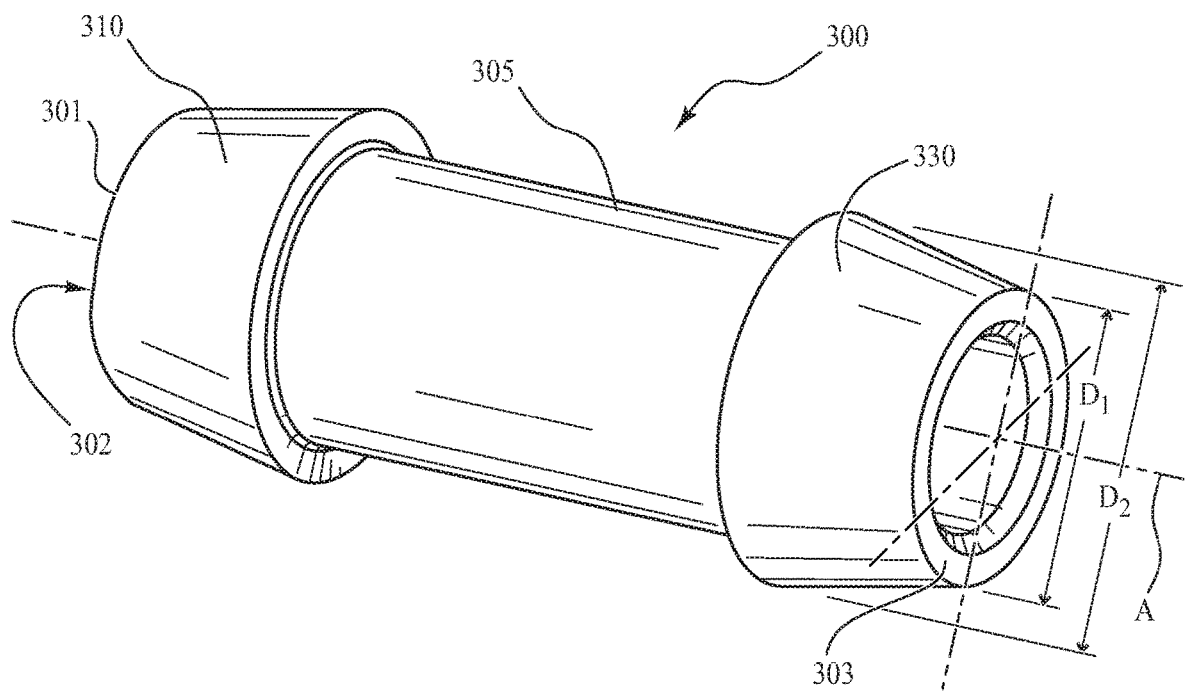
FIG. 6 is a perspective view of a coupler according to an embodiment.

FIG. 6 is a perspective view of a coupler 300 having a body 305, two ends 301, 303 and a lumen 302. The lumen 302 extends from the first end 301 through the body 305 to the second end 303 and may be centrally disposed within the coupler 300. In some embodiments, the coupler 300 may be solid and not have a lumen. The coupler 300 includes a first barb 310 at the first end 301 and a second barb 330 at the second end 303. Each barb 310, 330 has a tapering profile with a first diameter $D_1$ narrower than a second diameter $D_2$. The first barb 310 has the first diameter $D_1$ disposed toward the first end 301 of the coupler 300. The second barb 330 has the first diameter $D_1$ disposed toward the second end 303 of the coupler 300. In other words, the two barbs 310, 330 taper toward their respective ends 301, 303 where each barb 310, 330 is disposed.

The coupler 300 may be configured to couple to a catheter by inserting a portion of the coupler 300 into a lumen of the catheter. For instance, the first diameter $D_1$ of each barb 310, 330 may be sized smaller than a diameter of a lumen of a catheter to which the coupler 300 is configured to be coupled. The second diameter $D_2$ may be larger than a diameter of a lumen of the catheter. For example, with reference to the catheter of FIGS. 1A and 1B, in some embodiments, the first diameter $D_1$ of the first barb 310 is small enough to fit into the lumen 120 of the catheter 100, while the second diameter $D_2$ of the first barb 310 is large enough to at least minimally resist being inserted into the lumen 120 of the catheter 100. The material from which the catheter 100 is manufactured may be sufficiently flexible to expand over the first barb 310 to permit insertion of the first barb 310 into the lumen 120, and also sufficiently resilient that the portion of the catheter 100 which extends past the first barb 310 of the coupler 300 may tend to compress inward around the body 305 of the coupler 300. Along with the shape of the first barb 310, the compression of the catheter 100 may sufficiently resist tension to decouple the catheter 100 from the first barb 310 when the tension is applied to the coupled coupler 300 and catheter 100. The second barb 330 may be inserted into a replacement catheter (100' of FIG. 11) in a similar fashion. When thus coupled and with reference to catheters 100, 100' of FIG. 11, the coupler 300 may resist decoupling from the catheter 100 and the replacement catheter 100' to permit the catheter 100 to be drawn out of the body and the replacement catheter 100' is drawn into the body. The coupler 300 may provide sufficient tensile strength to avoid parting (breakage of the coupler 300 or decoupling from either catheter 100, 100') during the catheter replacement procedure. Emplacing the replacement catheter 100' by coupling it to the catheter 100 via the coupler 300 may be used instead of the potentially more invasive emplacement procedure used to initially place the catheter 100. In some embodiments, the coupler 300 may include one or more radiopaque markers (not shown) to facilitate emplacement.

Figure 7:
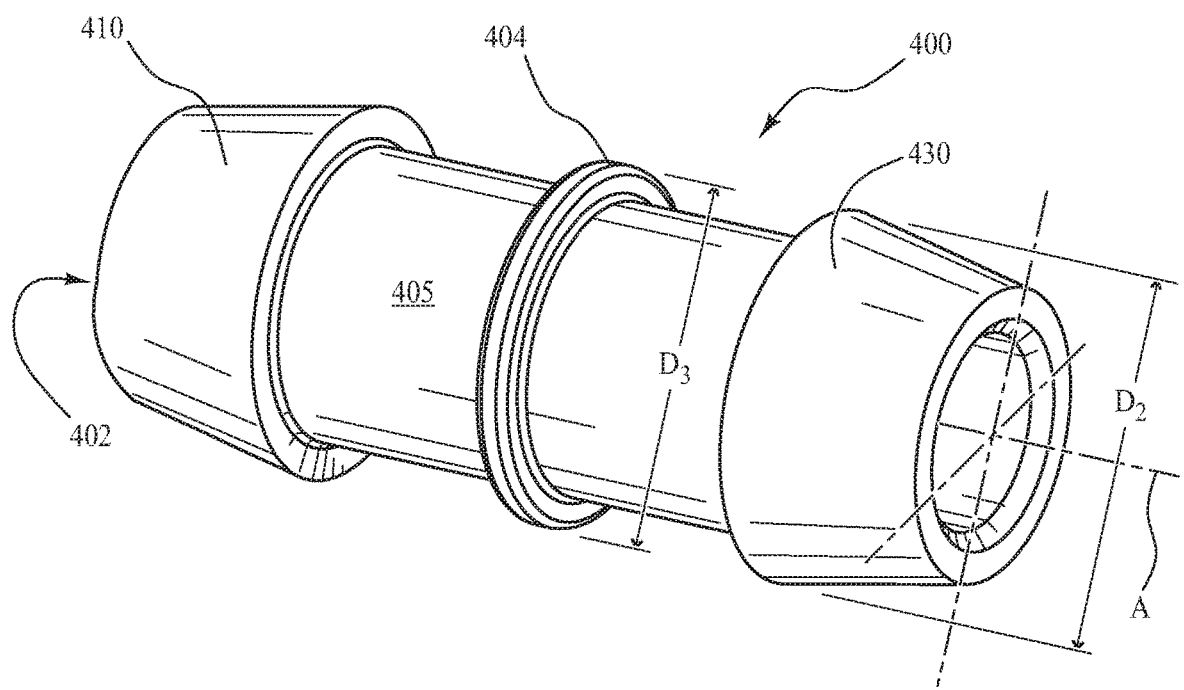
FIG. 7 is a perspective view of a coupler according to an embodiment.

FIG. 7 depicts an embodiment of a coupler 400 that resembles the coupler 300 described above in certain respects. Accordingly, like features are designated with like reference numerals, with the leading digit incremented to "4." For example, the embodiment depicted in FIG. 7 includes first barb 410 that may, in some respects, resemble the first barb 350 of FIG. 6. Relevant disclosure set forth above regarding similarly identified features thus may not be repeated hereafter. Moreover, specific features of the coupler 400 and related components shown in FIG. 6 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant description of such features apply equally to the features of the coupler 400 and related components depicted in FIG. 7. Any suitable combination of the features, and variations of the same, described with respect to the coupler 300 and related components illustrated in FIG. 6, can be employed with the coupler 400 and related components of FIG. 7, and vice versa. This pattern of disclosure applies equally to further embodiments depicted in subsequent figures and described hereafter, wherein the leading digits may be further incremented.

FIG. 7 is a perspective view of an embodiment of a coupler 400 similar to the coupler 300 of FIG. 6 and having a flange 404. A lumen 402, a first barb 410, and a second barb 430 are shown for reference. The flange 404 is disposed at or near a longitudinal midpoint of a body 405. In other words, in the illustrated embodiment, the flange 404 is approximately midway between the first barb 410 and the second barb 430. In the embodiment of FIG. 7, the flange 404 circumscribes the body 405. The flange 404 has a diameter $D_3$ approximately equal to the second diameter $D_2$ of either barb 410, 430. In another embodiment, the diameter $D_3$ of the flange 404 may exceed the second diameter $D_2$ of the barbs 410, 430. In an embodiment of the coupler 400 intended to replace the catheter 100 of one diameter with the replacement catheter 100' having a different diameter, the barbs 410, 430 may each have a diameter $D_2$ corresponding to the catheter 100, 100' to which each may be coupled. In such an embodiment, the flange 404 may include a taper to "step up" or "step down" from one catheter size to another catheter size. In some embodiments, the flange 404 may comprise a radiopaque marker.

Figure 8:
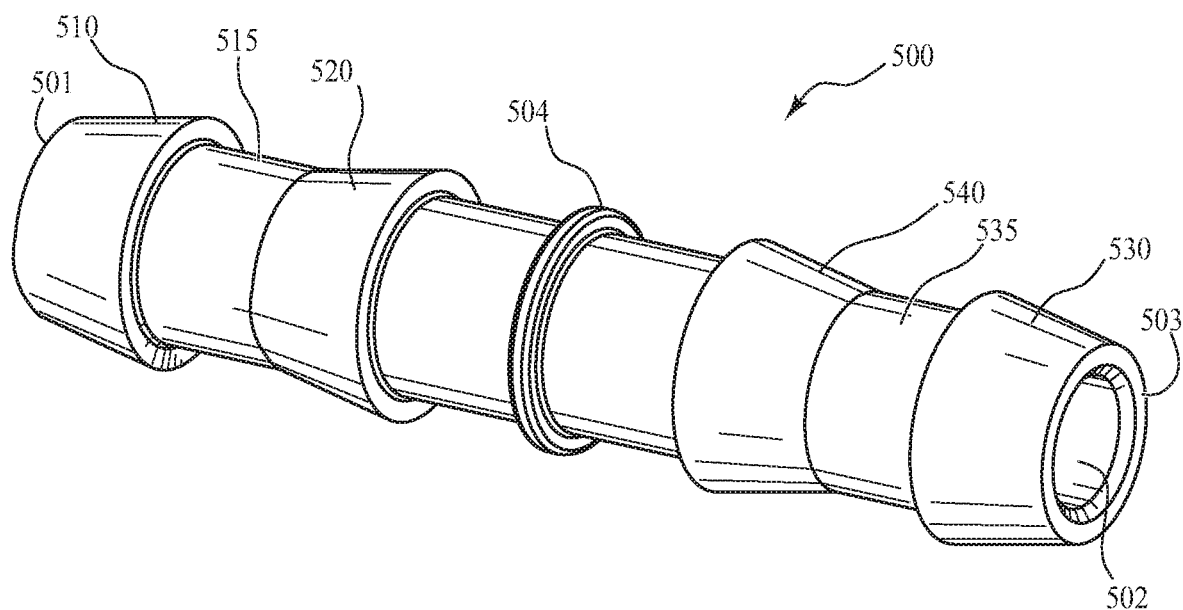
FIG. 8 is a perspective view of a coupler according to an embodiment.

FIG. 8 is a perspective view of an embodiment of a coupler 500 similar in some respects to the coupler 300 and the coupler 400 of FIGS. 6 and 7, respectively, having a plurality of barbs 510, 520, 530, 540 disposed toward either end 501, 503. The barbs 510, 520, 530, 540 disposed at the first and second ends 501, 503 and a lumen 502 are shown for reference. A first distal barb 510 may be disposed at or near the first end 501 of the coupler 500, and a first proximal barb 520 may be disposed somewhat proximally relative to the first distal barb 510. A first untapered region 515 may be disposed between the first distal barb 510 and the first proximal barb 520. Similarly, a second distal barb 530 may be disposed at or near the second end 503 of the coupler 500, with a second proximal barb 540 disposed somewhat proximally relative to the second distal barb 530, and a second untapered region 535 may be disposed between the second distal and second proximal barbs 530, 540. The additional barbs 520, 540 further engage with the catheter 100, 100' to help secure the coupler 400 to the catheters 100, 100'. In at least one embodiment, the coupler 500 may include a flange 504.

Figure 9:
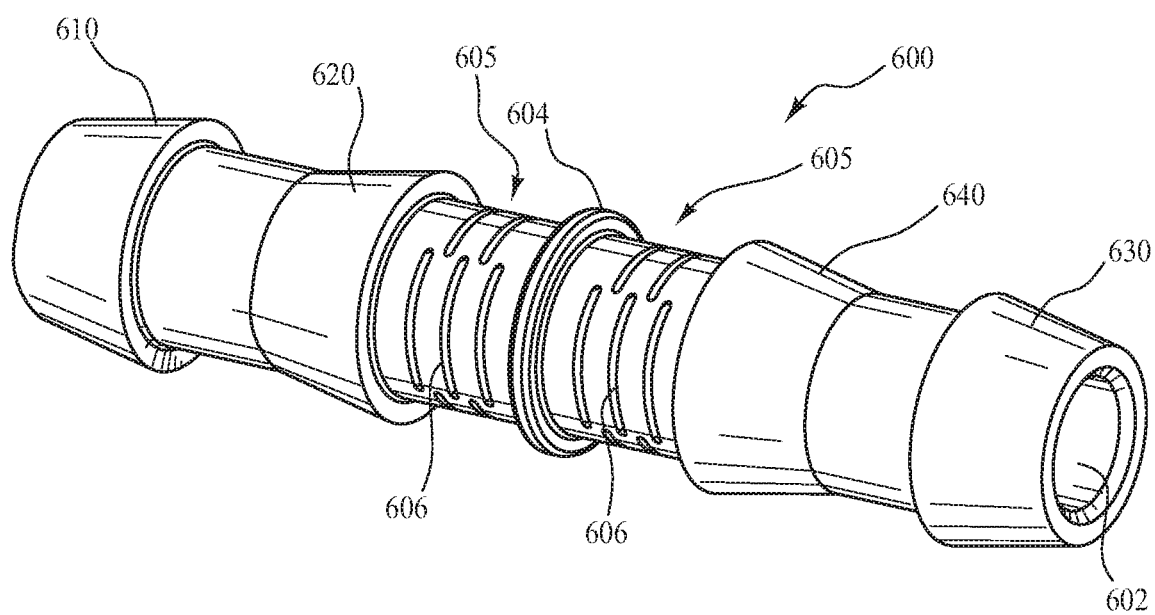
FIG. 9 is a perspective view of a coupler according to an embodiment.

FIG. 9 is a perspective view of an embodiment of a coupler 600 similar to the coupler 500 of FIG. 8 in certain respects and having a plurality of flex slots 606 in a central body portion 605. The flex slots 606 may extend along a portion of the circumference of the central body portion 605. First distal and proximal barbs 610, 620, second distal and proximal barbs 630, 640 and a lumen 602 are shown for reference. The central body portion 605 may comprise a plurality of the flex slots 606 to permit the coupler 600 to flex about the central body portion 605 while minimizing the risk of unintended deformation of the coupler 600. The flexibility of the central body portion 605 enables the coupler 600 to bend while the catheters 100, 100' are disposed within the patient. For example, as discussed in more detail below, the coupler 600 couples the catheter 100' and the replacement catheter 100' and as the catheter 100 is drawn out of the patient and the replacement catheter is drawn into the patient, the flexibility of the central body portion 605 help enable the coupler 600 navigate corners within the patient, e.g., the renal pelvis in the patient's kidney. The flexibility of the central body portion 605 has helps the coupler 600 maintain continuity between the catheters 100, 100' and minimize the possibility of the coupler 600 disconnecting from one of the catheters 100, 100' during the procedure. In at least one embodiment, a flange 604 may be disposed at the central body portion 605.

Figure 10:
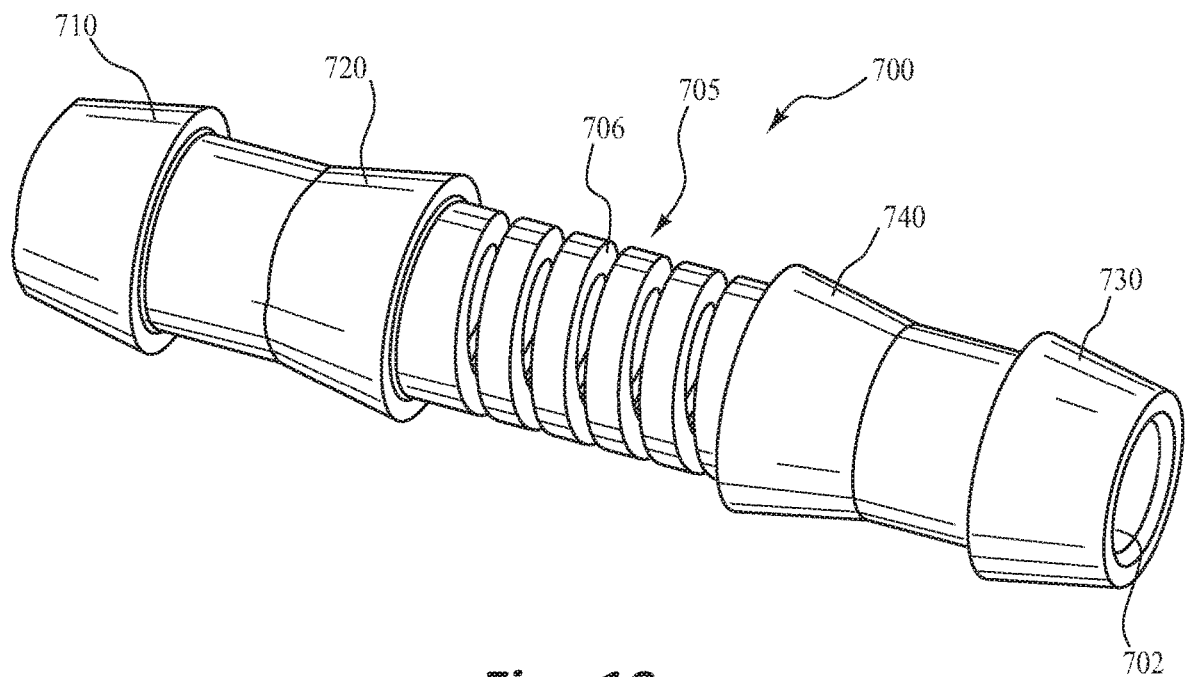
FIG. 10 is a perspective view of an embodiment of a coupler.

FIG. 10 is a perspective view of an embodiment of a coupler 700 similar in some respects to the coupler 600 of FIG. 9. First distal and proximal barbs 710, 720, second distal and proximal barbs 730, 740 and a lumen are shown for reference. The coupler 700 may have a flex coil 706 disposed in a central body portion 705 of the coupler 700. The flex coil 706 may permit the coupler 700 to flex about the central body portion 705 of the coupler 700 while minimizing the risk of unintended deformation of the coupler 700. The flexibility of the central body portion 705 enables the coupler 700 to bend while the catheters 100, 100' are disposed within the patient. For example, as discussed in more detail below, the coupler 700 couples the catheter 100' and the replacement catheter 100' and as the catheter 100 is drawn out of the patient and the replacement catheter is drawn into the patient, the flexibility of the central body portion 705 help enable the coupler 700 navigate corners within the patient, e.g., the renal pelvis in the patient's kidney. The flexibility of the central body portion 705 has helps the coupler 700 maintain continuity between the catheters 100, 100' and minimize the possibility of the coupler 700 disconnecting from one of the catheters 100, 100' during the procedure.

Figure 11:
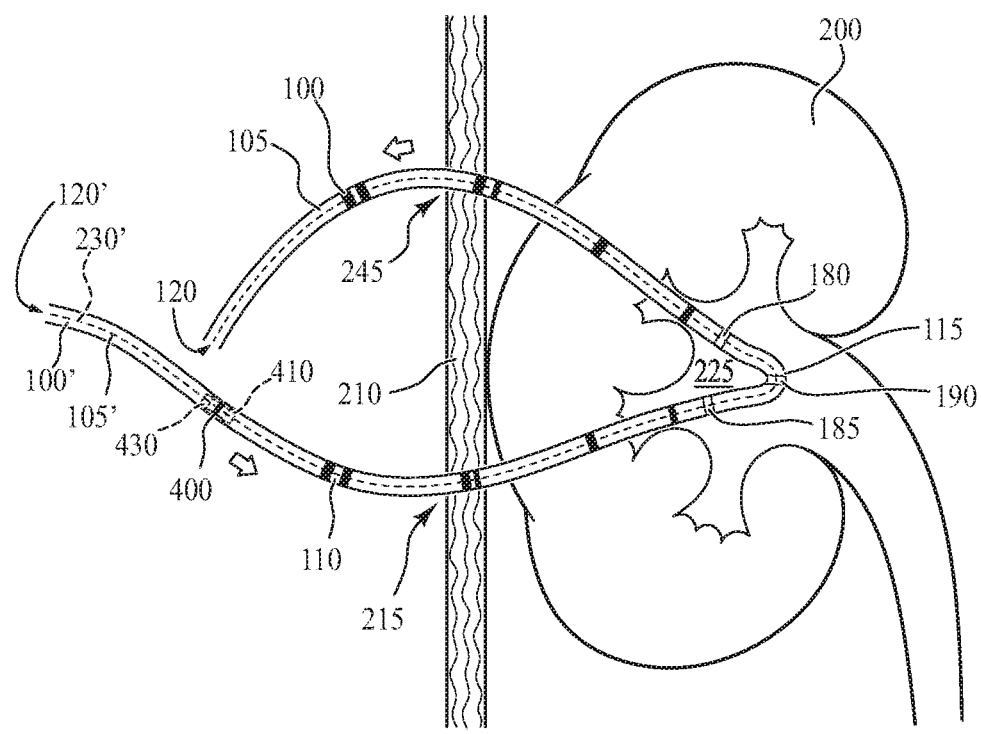
FIG. 11 depicts a first catheter having been disposed in a kidney and the first catheter coupled to a second catheter by a coupler.
Figure 12:
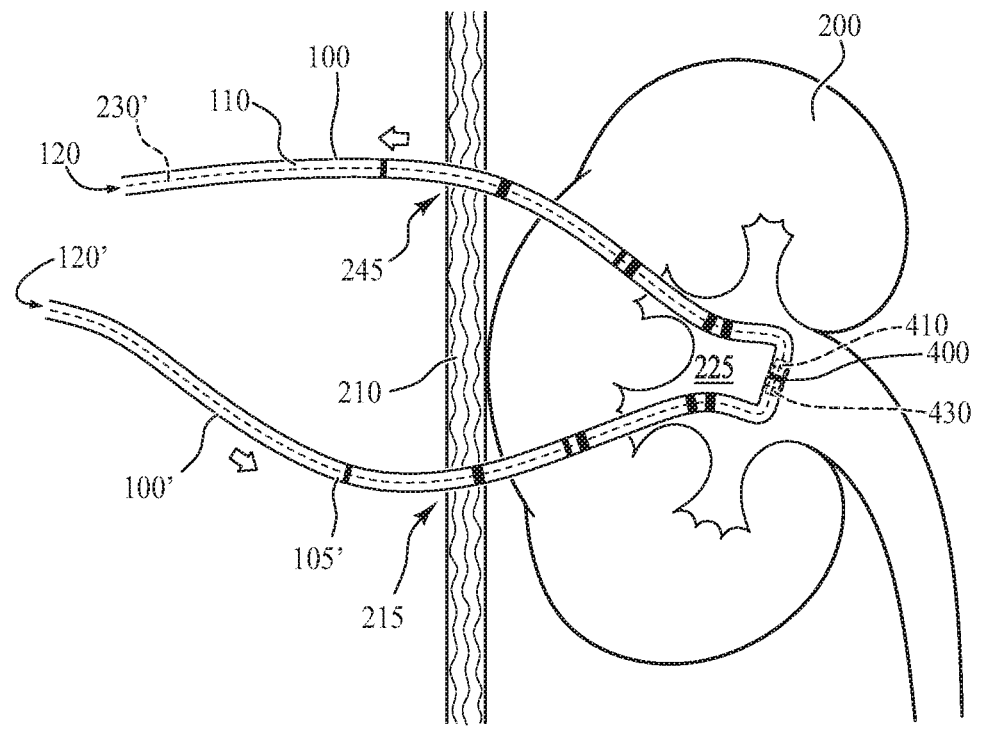
FIG. 12 depicts a partially completed replacement of the first catheter with the second catheter.

FIGS. 11-14 illustrate of an example of a procedure where a first catheter, such as catheter 100 has been disposed in the kidney 200 and the catheter 100 is to be replaced by a second catheter, such as replacement catheter 100'. The first catheter may be similar to the drainage catheter 100 or may be a pigtail drainage catheter. The first catheter and the second catheter may or may not include lead-in portions, similar to the lead-in portions 130 of catheter 100 described in FIGS. 1-5. FIG. 11 illustrates catheter 100 coupled to replacement catheter 100' by the coupler 400 of FIG. 7, which is used as example, but it is within the scope of the disclosure to use any of the couplers described herein. FIG. 12 is an illustration showing a partially completed replacement of the catheter 100. With respect to FIGS. 11-12, a kidney emplacement is shown; however, other catheter replacement scenarios in other parts of the body are within the scope of this disclosure. The catheter 100 may have been emplaced as described in connection with FIGS. 2-5 or a pigtail catheter may be emplaced. Prior to replacement, the catheter 100 may be cut or otherwise detached from any accoutrement external to the patient, such as the connector 265.

The coupler 400 may be used to facilitate replacement of the catheter 100 with the replacement catheter 100'. The coupler 400 may be coupled to the proximal tube segment 110 of the catheter 100 by inserting the first barb 410 of the coupler 400 in the lumen 120 of the proximal tube segment 110 of the catheter 100. The second barb 430 of the coupler 400 may be inserted into a lumen 120' of a distal tube segment 105' of the replacement catheter 100'. In some embodiments, if the distal tube segment 105' of the replacement catheter 100' includes a tapered lead-in portion, the lead-in portion may be removed (cut off) before inserting the coupler 400 into the lumen 120'. The coupler 400 may be coupled to either the catheter 100 or the replacement catheter 100' first, then coupled to the other catheters 100, 100'.

A guidewire 230' may be inserted into the lumens 120, 120', 402 of the catheters 100, 100' and the coupler 400. With the distal tube segment 105' of the replacement catheter 100' coupled via the coupler 400 to the proximal tube segment 110 of the catheter 100, the distal tube segment 105 of the catheter 100 may be drawn out of the patient. As the catheter 100 is drawn out of the patient, the replacement catheter 100' is pulled through the first insertion site 215, through the renal pelvis 225, and through the second insertion site 245. Radiopaque marker bands 180', 185', 190' disposed at an arcuate end portion 115' of the replacement catheter 100' may facilitate placement of the arcuate end portion 115' in the renal pelvis 225. In FIG. 12, the replacement process is illustrated with the coupler 400 in the renal pelvis 225. While the coupler 400 is shown with no flex, in at least some embodiments, the coupler 400 may be of a type that may flex as the coupler 400 passes through the renal pelvis 225 or around other paths.

Figure 13:
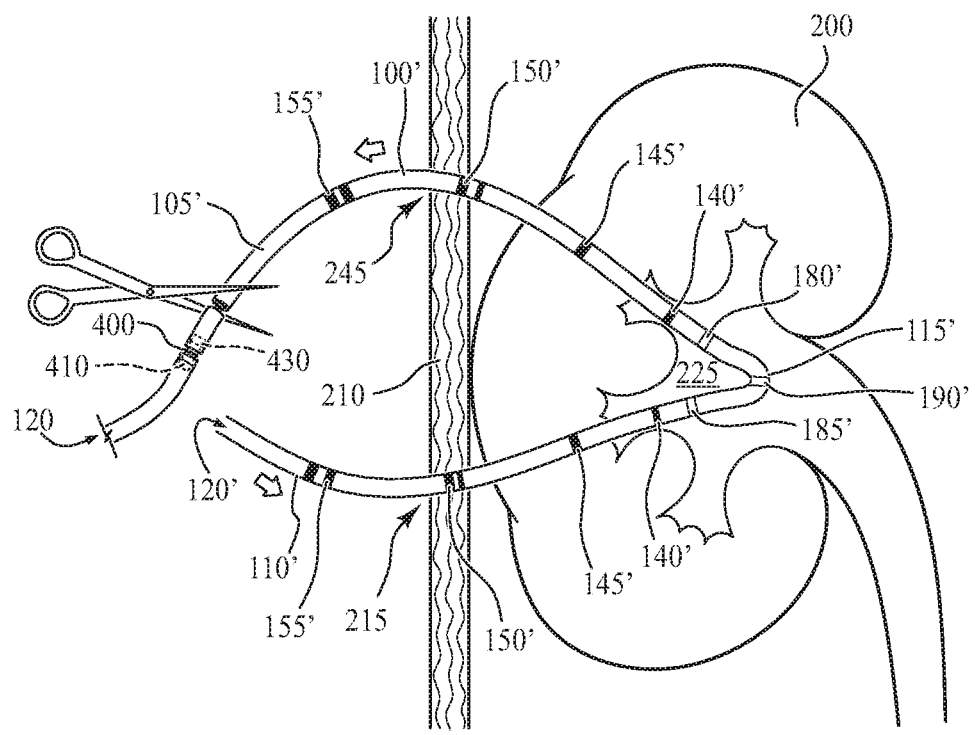
FIG. 13 depicts the second catheter having been fully drawn into place utilizing the coupler.

FIG. 13 is an illustration of the replacement catheter 100' having been fully drawn into place utilizing the coupler 400 following pre-existing pathways created by the placement of the first catheter. In an example where a pigtail catheter is used and only there is only an existing pathway into the kidney 200 and not out of the kidney 200, a similar method may be used to create a pathway for the replacement catheter 100' to exit the kidney. The coupler 400 may be detached from the distal tube segment 105' of the replacement catheter 100' by cutting the distal tube segment 105' near the coupler 400 with an appropriate tool. The coupler 400 may remain coupled to the proximal tube segment 110 of the catheter 100 for ease of disposal and to prevent risk of losing the coupler 400 (such as the fully detached coupler falling to the floor or into the patient's bedding or clothing). Either before or after detaching the coupler 400 from the replacement catheter 100', the radiopaque marker bands 180', 185', 190' associated with the arcuate end portion 115' of the replacement catheter 100', as well as depth markers 140', 145', 150', 155' along a proximal tube segment 110' and the distal tube segment 105' may be used to confirm the position of the replacement catheter 100' such that the arcuate end portion 115' is disposed in the renal pelvis 225.

Figure 14:
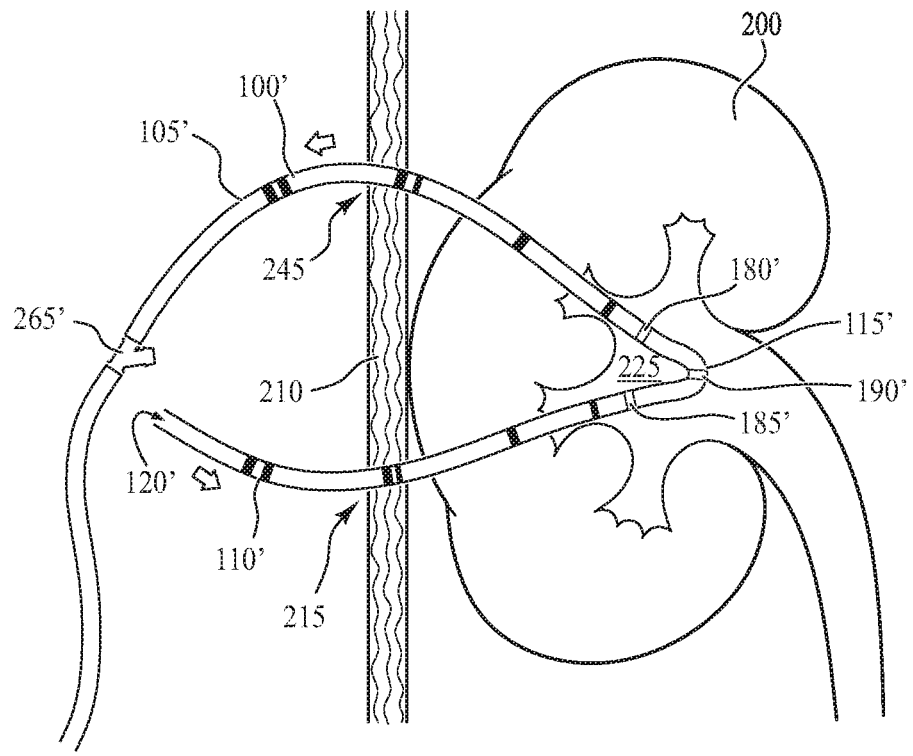
FIG. 14 depicts the second catheter having been disposed within the kidney utilizing the coupler and prepared for coupling to an external connector external to the skin.

FIG. 14 is an illustration of the replacement catheter 100' having been disposed utilizing the coupler 400 and prepared for coupling to an external connector 265' external to the skin 210. The connecter 265' may be first coupled to the distal tube segment 105' after the coupler 400 has been detached, and then coupled to the proximal tube segment 110', as shown. Alternatively, the connector 265' may be coupled first to the proximal tube segment 110' and then to the distal tube segment 105'. The tube segments 105', 110' may be connected to the connector 265', which in turn is connected to a drainage bag or other receptacle/medical service device (not shown) for collecting the drained material.

Figure 15:
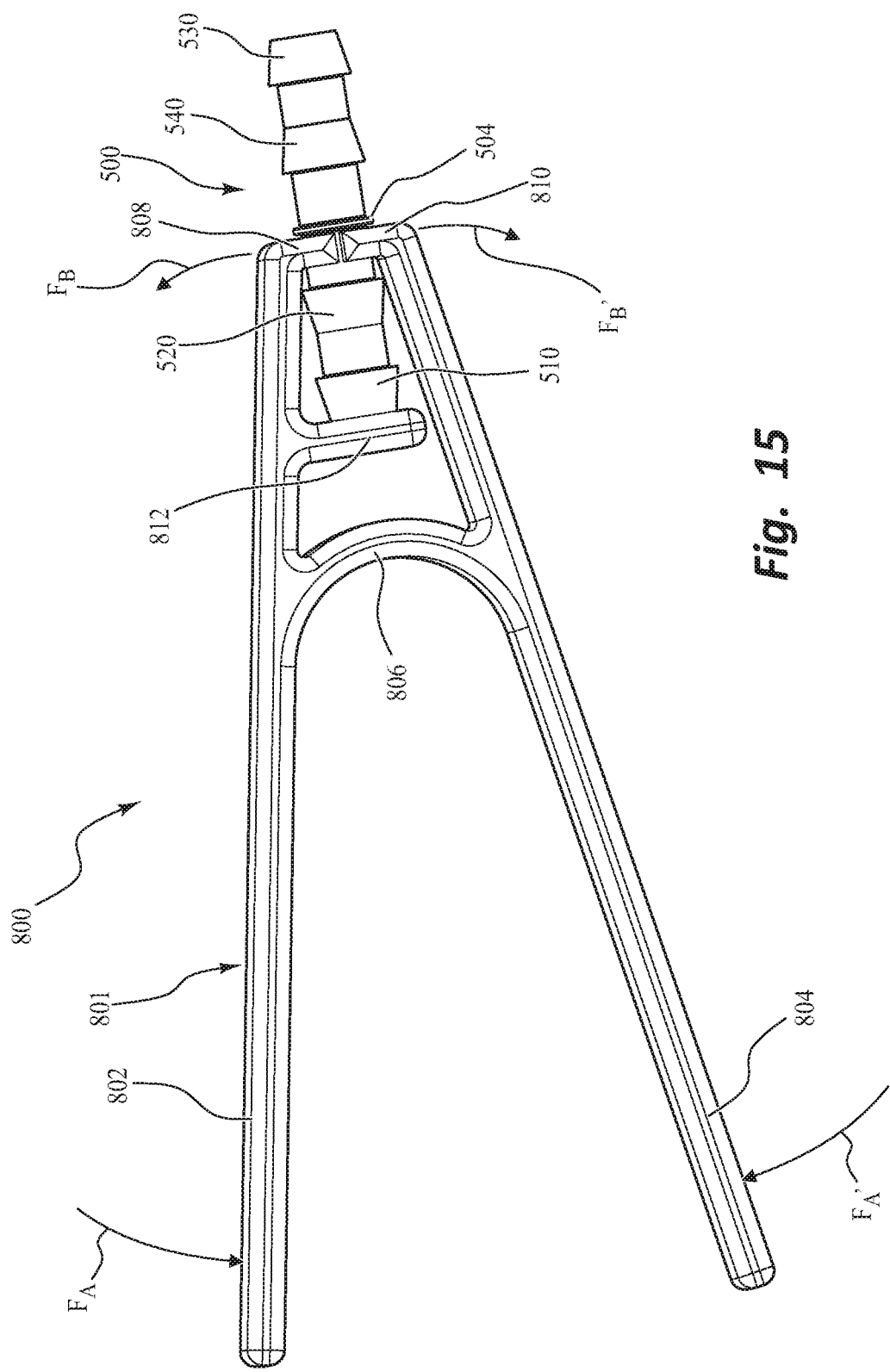
FIG. 15 is a perspective view of a coupler delivery system according to an embodiment.

FIG. 15 illustrates a coupler delivery system 800 according to an embodiment of the present disclosure. The coupler delivery system 800 may include a coupler handle 801 and a coupler 500. The coupler handle 801 may be a clamp-grip. The coupler 500 may be a coupler of any type disclosed herein. The first distal and proximal barbs 510, 520 and the second distal and proximal barbs 530, 540 of the coupler 500 are shown. The coupler 500 may include a flange 504. The coupler handle 801 may be manufactured of any suitable material compatible with the coupler 500. The coupler handle 801 may be formed as a single-piece tool, for example, by press molding, injection molding, or any other appropriate method. In another embodiment, the coupler handle 801 may be formed as a multi-piece tool wherein each component may be of any appropriate material and then assembled to form the coupler handle 801.

In the illustrated embodiments, the coupler handle 801 comprises a first handle 802, a second handle 804, a torsion spring 806, a first clamp jaw 808, a second clamp jaw 810, and a backstop 812. The first and second handles 802, 804 may be held in a spread configuration by the torsion spring 806. The torsion spring 806 may also press the first clamp jaw 808 and the second clamp jaw 810 toward or against each other. The coupler 500 may be seated between the first and second clamp jaws 808, 810 such that the coupler 500 buts against the backstop 812. The flange 504 may serve to prevent the coupler 500 from moving rearward toward the torsion spring 806 as pressure may be applied to couple the coupler 500 to the catheter 100, 100'. The backstop 812 may be configured with a pin (not shown) that may protrude into the lumen of the coupler 500. The backstop 812 may be configured with a recessed ring (not shown) in the face of the backstop 812 proximal to the first and second clamp jaws 808, 810. The pin and/or recessed ring may assist in keeping the coupler 500 stable as pressure is applied to couple the coupler 500 to the catheter 100, 100'.

In some embodiments, the coupler 500 does not have a backstop to prevent axial movement. Axial movement in this embodiment may be limited by the flange 504 and the barb 520 when the flange 504 or the barb 520 engage with the first and second clamp jaws 808, 810.

The first and second handles 802, 804 may be pressed toward each other in opposing directions $F_A$, $F_A'$, which may simultaneously cause the first and second clamp jaws 808, 810 to move in opposing directions $F_B$, $F_B'$ and thereby release the coupler 500 from the coupler handle 801. The coupler delivery system 800 may be provided fully assembled having the coupler 500 pre-coupled to the clamp-grip 801 from a manufacturer. In another embodiment, the coupler 500 may be coupled to the coupler handle 801 immediately prior to and preparatory to coupling the coupler 500 to the catheter 100, 100'.

FIG. 16A is an exploded perspective view of a coupler delivery system 900, according to another embodiment, including a coupler 500 and a coupler handle 901. As with the embodiment of FIG. 15, the coupler 500 may be of any type disclosed herein. FIG. 16B is an assembled perspective view of the coupler delivery system 900 of FIG. 16A. With respect to FIGS. 16A and 16B, the first distal and proximal barbs 510, 520, the second distal and proximal barbs 530, 540 are shown for reference. The coupler 500 may include the flange 504. The coupler handle 901 may further include a plurality of ribs 910 and voids 912.

The coupler handle 901 may have a snap fitting 902 to secure the coupler 500 to the coupler delivery system 900. The snap fitting 902 comprises a plurality of arms 904, with each arm 904 having a lug 906. The lug 906 of each arm 904 may be configured to snap over the first distal barb 510 of the coupler 500 so as to couple the coupler 500 to the coupler handle 901. The snap fitting 902 may be sufficiently resilient to retain the coupler 500 on the coupler handle 901 against the application of lateral forces, and may also be sufficiently flexible to allow the snap fitting 902 to release the coupler 500 from the coupler handle 901 at the application of a predetermined lateral force. In other words, the amount of force to disengage the coupler handle 901 from the coupler 500 is less than the amount of force to remove the coupler 500 from the lumen of one of the catheters 100, 100'. The medical care giver may also squeeze the distal tube segment 105, 105' of the catheter 100, 100' where the catheter 100, 100' is coupled to the coupler 500 to ensure the catheter 100, 100' and the coupler 500 remain coupled together as lateral force is applied to the coupler handle 901 to release the coupler 500 from the coupler handle 901.

The coupler handle 901 may include a stabilizing pin 908 which fits into the lumen of the coupler 500 to provide stability while the coupler 500 is being coupled to the catheter 100, 100'. The coupler handle 901 may be manufactured of any material suitable to the coupling 500.

As noted above, the coupler handle 901 may include a plurality of the ribs 910 and the voids 912 to provide a gripping surface for the medical care giver. The gripping surface may be beneficial for medical care givers if their hands are wet or if the gloves they are wearing are wet. The coupler 500 may be coupled to the coupler handle 901 during manufacture. In another embodiment, the coupler 500 may be fitted to the coupler handle 901 immediately prior to and in preparation of the catheter replacement procedure.

Figure 17A:
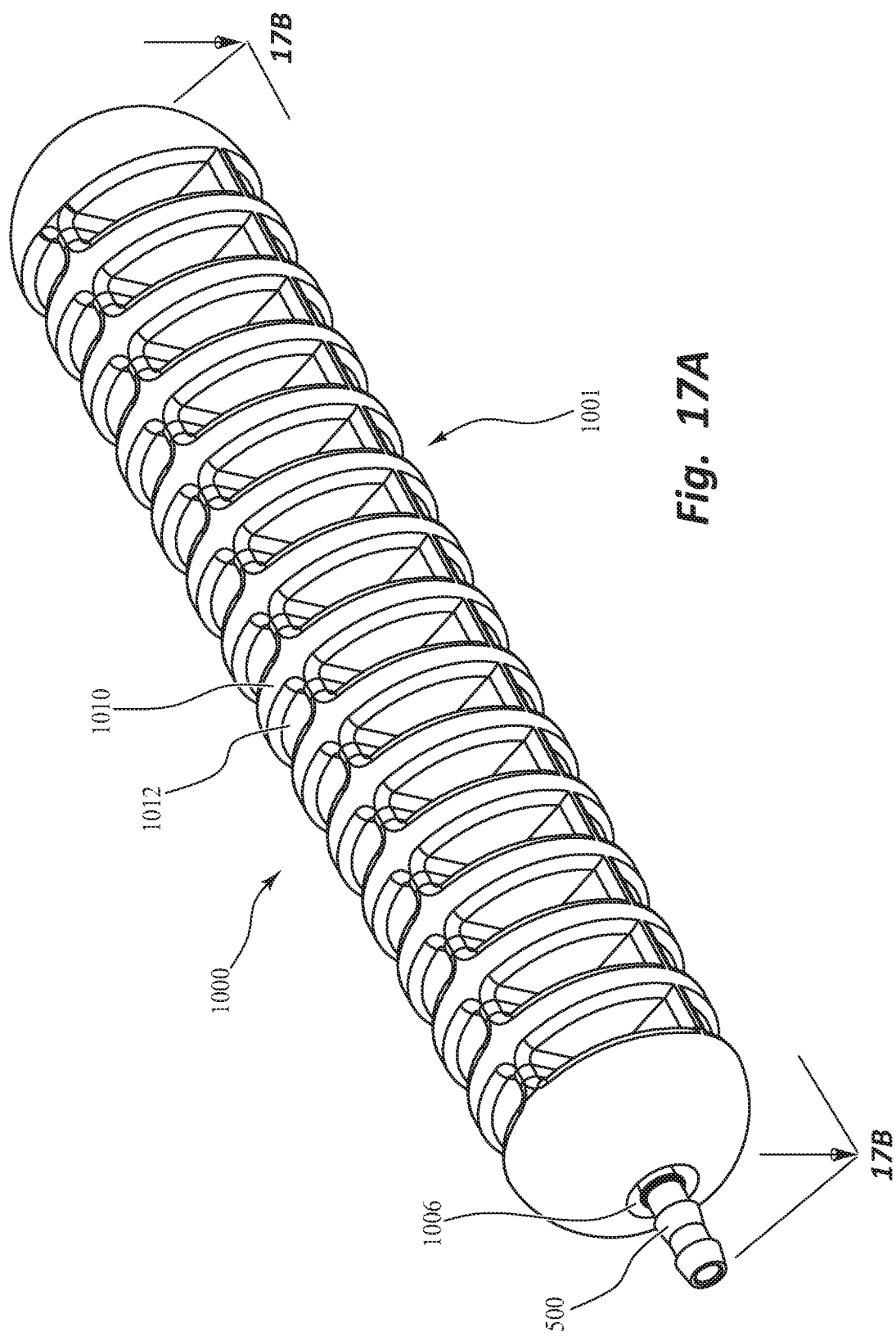
FIG. 17A is a perspective view of a coupler delivery system is according to an embodiment.

FIG. 17A is a perspective view of a coupler delivery system 1000 similar in some respects to the coupler delivery system 900 of FIG. 16A. The coupler delivery system 1000 may comprise a coupler handle 1001 having a well 1006. The coupler handle 1001 may include a plurality of ribs 1010 and voids 1012 to provide a gripping surface for the medical care provider. The well 1006 of the coupler handle 1001 may be configured to receive and hold the coupler 500 to facilitate coupling the coupler 500 to the catheter 100, 100'. FIG. 17A shows cross-sectional plane 17B-17B for FIG. 17B.

Figure 17B:
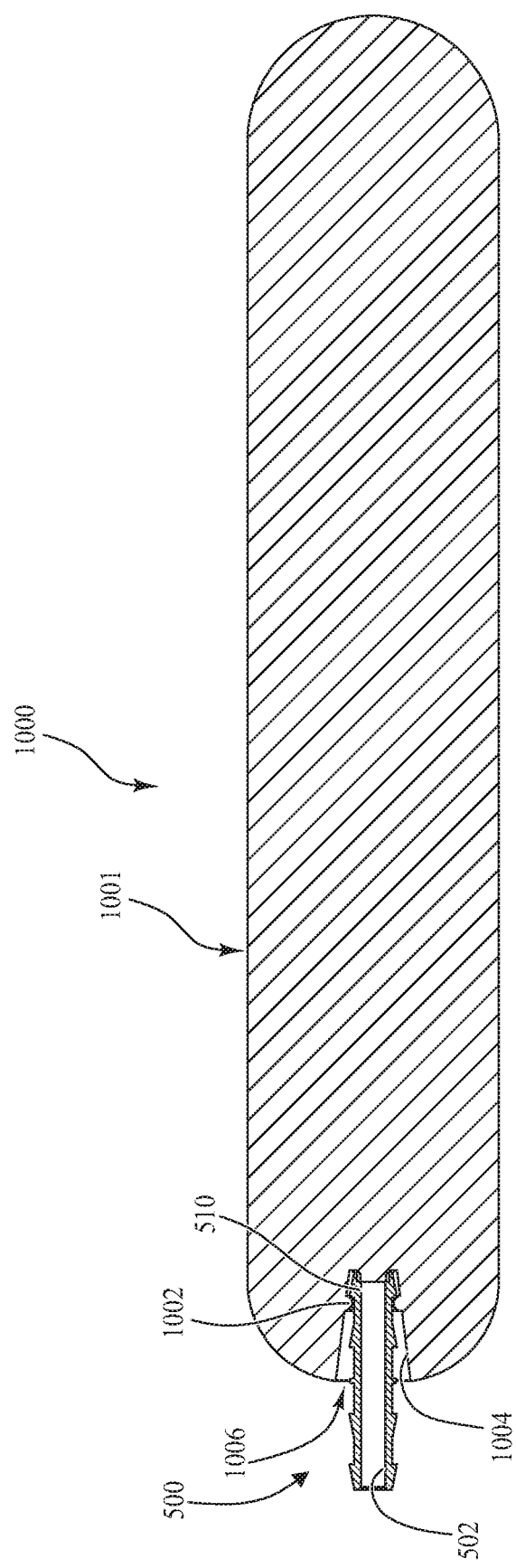
FIG. 17B is a cross-sectional side view of the coupler delivery system of FIG. 17A.

FIG. 17B is a cross-sectional side view of the coupler delivery system 1000 of FIG. 17A. The first distal barb 510 and the lumen 502 of the coupler 500 are shown for reference. The well 1006 of the coupler handle 1001 may include one or more lugs 1002. The lugs 1002 may be configured to snap over the first distal barb 510 of the coupler 500 so as to couple the coupler 500 to the coupler handle 1001. The lugs 1002 may be configured to retain the coupler 500 under lateral forces, and to permit the coupler 500 to decouple from the coupler handle 1001 with the application of a predetermined lateral force. In other words, the amount of force to disengage the coupler handle 1001 from the coupler 500 is less than the amount of force to remove the coupler 500 from the lumen of one of the catheters 100, 100'. The well 1006 of the coupler handle 1001 may include an inner wall 1004 having a taper to accommodate flexing of the coupler 500 as lateral force is applied to decouple the coupler 500 once the coupler 500 has been coupled to the catheter 100, 100'.

Figure 18A:
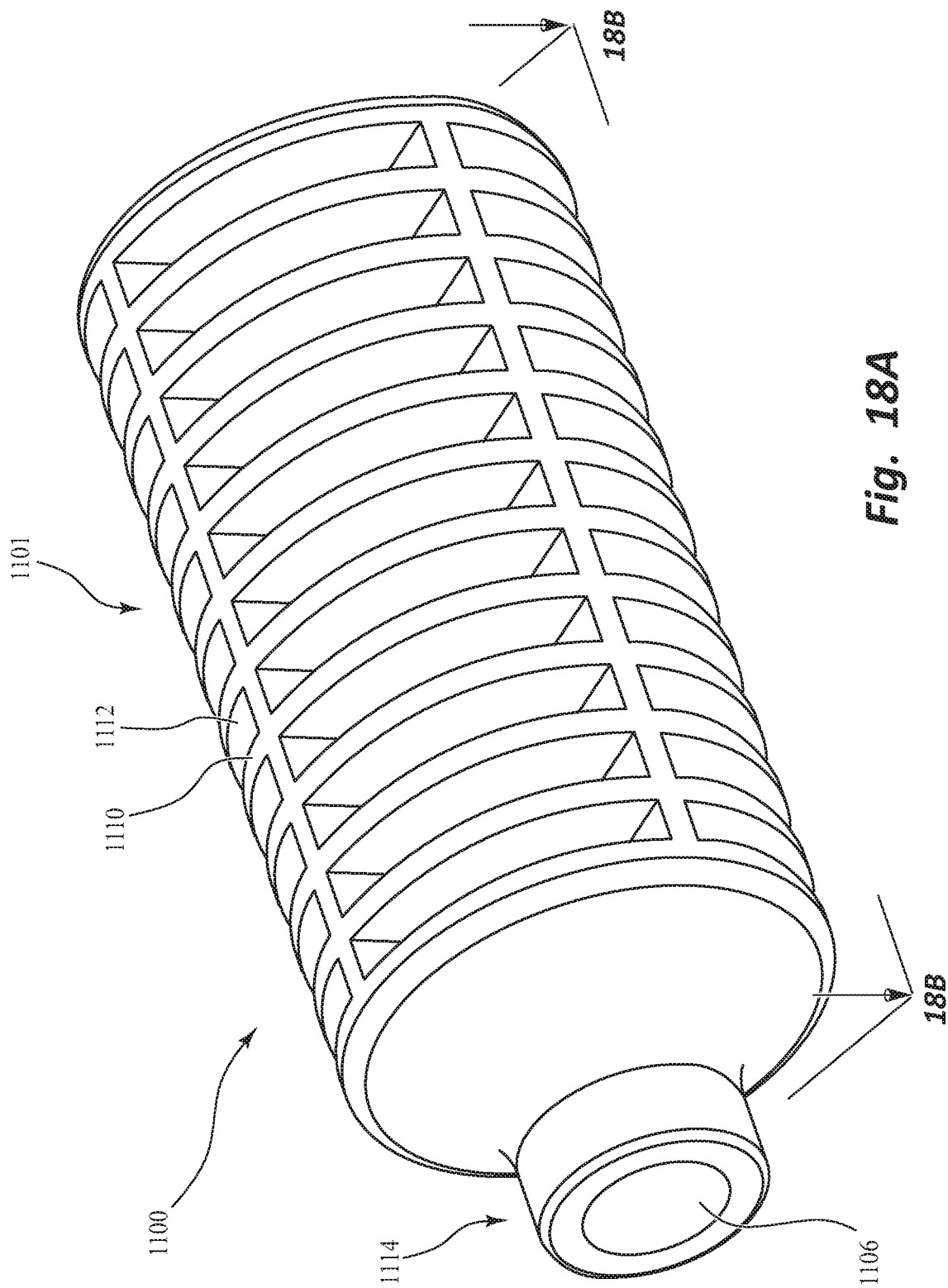
FIG. 18A is a perspective view of a coupler delivery system according to an embodiment.

FIG. 18A is a perspective view of a coupler delivery system 1100 similar to the coupler delivery system 1000 of FIG. 17A in some respects. The coupler handle 1101 may have ribs 1110 and voids 1112 as previously described. The coupler handle 1101 may also include an annular ring 1114 and a well 1106, both disposed at an end of the coupler handle 1101. The well 1106 may be a centrally disposed feature of the annular ring 1114. In other words, the annular ring 1114 may be located at one end of the coupler handle 1101, and may have an opening (the well 1106). As with the coupler delivery system 1000 of FIG. 17A, a coupler (not shown) of any type disclosed herein may be coupled to the coupler handle 1101, such as by fitting into the well 1106 of the annular ring 1114. FIG. 18A shows cross-sectional plane 18B-18B for FIG. 18B.

Figure 18B:
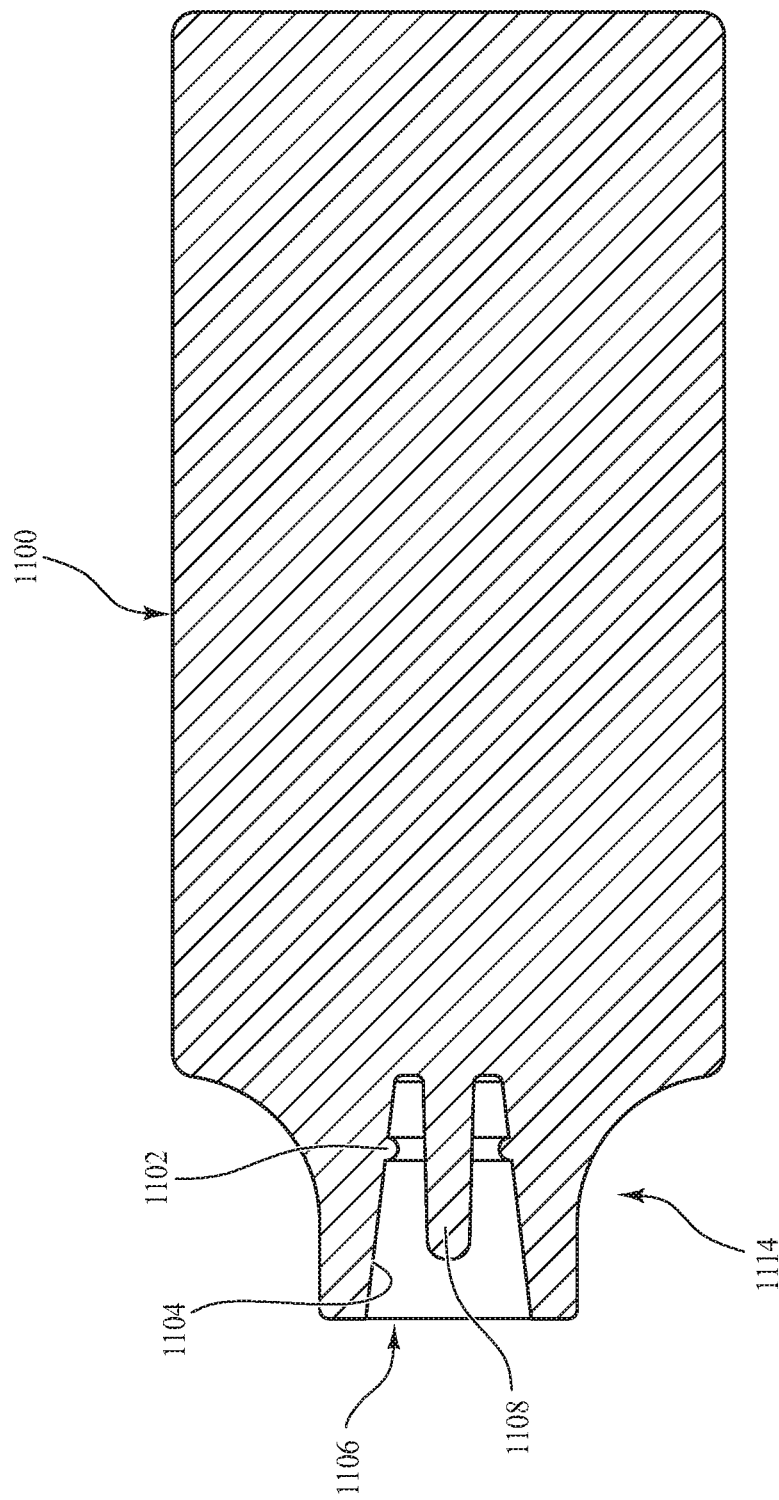
FIG. 18B is a side cross-sectional view of the coupler delivery system of FIG. 18A.

FIG. 18B is a side cross-sectional view of the coupler delivery system 1100 of FIG. 18A. The well 1106 of the annular ring 1114 may have a tapered inner wall 1104. One or more lugs 1102 may be disposed at the inner wall 1104. The well 1106 may include a stabilizing pin 1108.

Figure 19:
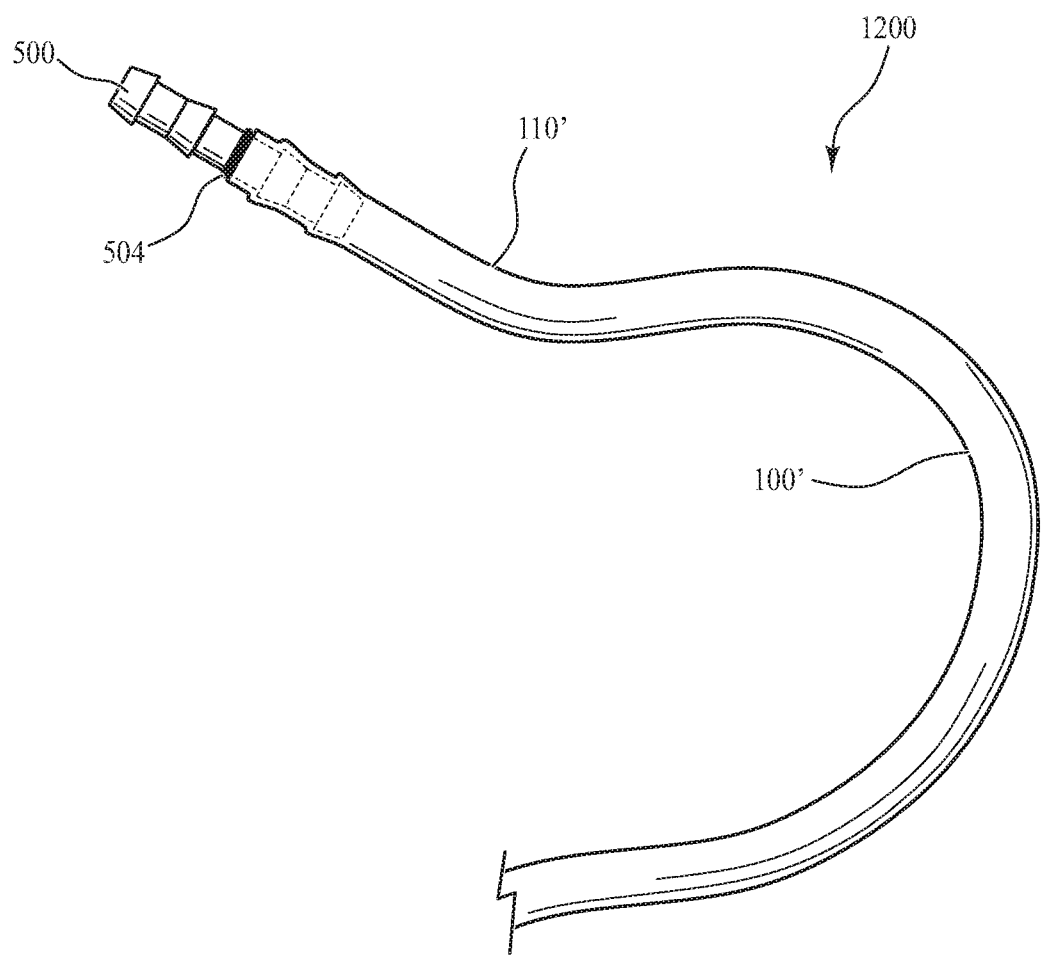
FIG. 19 is side view of a coupler delivery system having the coupler pre-coupled to a second catheter.

FIG. 19 is side view of a coupler delivery system 1200 having a coupler 500 pre-coupled to the replacement catheter 100'. The coupler 500 may be a coupler of any type disclosed herein. The coupler 500 may be coupled to the proximal tube segment 110' of the replacement catheter 100' at the time of manufacture, or at a time prior to packaging for delivery into a health care system. The coupler 500 may include the flange 504. When replacing an emplaced catheter 100 (see FIGS. 11-14), a health care giver may couple the exposed portion of the coupler 500 to the proximal tube segment 110 of the catheter 100. The guidewire 230' may be inserted, and the replacement catheter 100' may proceed as outlined above. Once the replacement catheter 100' is emplaced, the proximal tube segment 110 of the catheter 100 may be cut to detach the coupler 500 and the catheter 100 from the emplaced replacement catheter 100'.

A coupler delivery system according to any of the embodiments of this disclosure may be delivered to a medical care facility in the form of a sealed and sterile kit (not shown). By way of example without limitation, the kit may include the coupler delivery system, a guidewire, site preparation materials (such as, e.g., a cleaning swab), a shear, disposal materials, etc. The kit may include a replacement catheter (the coupler delivery system 1200 includes a catheter as a component of the coupler delivery system 1200). The kit may also include a connector. The kit may also include further components which may couple to the connector for a particular purpose. A kit may be provided with a coupler delivery system and additional components as may be specially ordered by the health care system.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially straight" is recited with respect to a feature, it is understood that in further embodiments, the feature can have a precisely straight configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A catheter exchange system, comprising:
   a second catheter comprising:
      a tubular body having a first end and a second end; and
      a lumen extending from the first end of the tubular body to the second end of the tubular body; and
   a coupler comprising:
      a body having a first end and a second end; and
      at least one barb disposed at the first end of the coupler and at least one barb disposed at the second end of the coupler,
      wherein the coupler is configured to couple to a first catheter and the second catheter by coupling the first end of the coupler to the first catheter and coupling the second end of the coupler to the second catheter, wherein the coupler is configured to use during catheter replacement procedure to replace the first catheter with the second catheter, wherein the first catheter is configured to currently be disposed in a patient,
      wherein the coupler has a central body portion that is disposed between the at least one barb disposed on the first end and the at least one barb disposed on the second end, wherein the central body portion is flexible and allows the central body portion to bend, and wherein the central body portion includes a plurality of flex slots disposed in the body of the coupler that partially extend circumferentially around the central body portion.

2. The catheter exchange system of claim 1, wherein the first end of the coupler is coupled to the first catheter by inserting the first end of the coupler into a lumen of the first catheter.

3. The catheter exchange system of claim 2, wherein the second end of the coupler is coupled to the second catheter by inserting the second end of the coupler into the lumen of the second catheter.

4. The catheter exchange system of claim 1, wherein the coupler further comprises at least two barbs at the first end and at least two barbs at the second end.

5. The catheter exchange system of claim 1, further comprising a coupler handle, wherein the coupler handle is configured to grip the coupler and enable a user to insert the coupler into one of a lumen of the first catheter and the lumen of the second catheter.

6. The catheter exchange system of claim 5, wherein the coupler handle disengages from the coupler with a force less than an amount of force to remove the coupler from the lumen of the catheter one of the lumen of the first catheter and the lumen of the second catheter.

7. The catheter exchange system of claim 5, wherein the coupler handle includes a plurality of arms that extend from the coupler handle to grip the barbs of the coupler, and
wherein each arm includes a lug that engages with the barbs of the coupler forming a snap fit between the coupler handle and the coupler.

8. The catheter exchange system of claim 5, wherein the coupler handle includes a well that grips the coupler, and
wherein the well includes a lug that engages with the barbs of the coupler forming a snap fit between the coupler handle and the coupler.

9. The catheter exchange system of claim 1, wherein the coupler is pre-coupled to the second catheter.

10. A method for exchanging a first catheter disposed within a patient with a second catheter, the method comprising:
coupling a first end of a coupler to the first catheter;
coupling a second end of the coupler to the second catheter, such that the first catheter is coupled to the second catheter via the coupler; and
removing the first catheter from the patient and advancing the second catheter within the patient by displacing the first catheter, such that the displacement of the first catheter removes the first catheter from the patient and simultaneously advances the second catheter within the patient.

11. The method of claim 10, wherein coupling the first end of the coupler to the first catheter is accomplished by inserting the first end of the coupler into a lumen of the first catheter.

12. The method of claim 10, wherein coupling the second end of the coupler to the second catheter is accomplished by inserting the second end of the coupler into a lumen of the second catheter.

13. The method of claim 10, further comprising inserting a guidewire through the first catheter, the coupler, and the second catheter.

14. A catheter kit comprising:
a second catheter that includes a lumen extending from a first end to a second end of the catheter; and
a coupler that includes barbs disposed at least at a first end and a second end of the coupler,
wherein the coupler is configured to couple to a first catheter previously disposed in a patient and the second catheter by coupling the first end of the coupler to the first catheter and coupling the second end of the coupler to the second catheter,
wherein the coupler has a central body portion that is disposed between the at least one barb disposed on the first end and the at least one barb disposed on the second end, and
wherein the central body portion is flexible and allows the central body portion to bend.

15. The catheter kit of claim 14, further comprising a coupler handle coupled to the coupler that is configured to be detached from the coupler with a predetermined amount of force.

16. The catheter kit of claim 14, wherein the coupler is pre-coupled to the catheter.

17. The catheter exchange system of claim 1, wherein the central body portion comprises a flange with a plurality of flex slots disposed on both sides of the flange.

* * * * *